United States Patent
Burnie

(12) 
(10) Patent No.: US 6,627,730 B1
(45) Date of Patent: Sep. 30, 2003

(54) STAPHYLOCOCCAL ABC TRANSPORTER PROTEIN

(75) Inventor: James Peter Burnie, Alderley Edge (GB)

(73) Assignee: NeuTec Pharma PLC, Manchester (GB)

( * ) Notice: Subject to any disclaimer, the term of this patent is extended or adjusted under 35 U.S.C. 154(b) by 0 days.

(21) Appl. No.: 09/672,494

(22) Filed: Sep. 29, 2000

Related U.S. Application Data

(63) Continuation of application No. PCT/GB99/00939, filed on Mar. 25, 1999.

(30) Foreign Application Priority Data

Mar. 31, 1998 (GB) ................................................ 9806762

(51) Int. Cl.[7] ........................ A61K 38/00; A61K 39/00; C07K 16/00
(52) U.S. Cl. ...................... 530/326; 530/327; 530/328; 530/329; 530/330; 530/350; 424/190.1
(58) Field of Search ................................. 530/300, 330, 530/329, 326, 350; 424/184.1, 185.1, 190.1, 234.1, 243.1

(56) References Cited

U.S. PATENT DOCUMENTS 6,013,494 A * 1/2000 Nakamura et al.
6,300,094 B1 * 10/2001 Warren et al.
6,380,370 B1 * 4/2002 Doucette-Stamm et al.

FOREIGN PATENT DOCUMENTS

EP 0 786 519 1/1997
WO WO/98/01154 1/1998

OTHER PUBLICATIONS

Berglindh et al, Gen Seq. Database Accession No. AAW20224, Jul. 9, 1997.*
Leimbach et al, Swiss Prot. Database Accession No. Q09221, Nov. 1, 1995.*
Donnelly et al. PIR Database Accession No. S30974, Sep. 30, 1993.*
Hoshino et al. PIR Database Accession No. E36125, Mar. 31, 1992.*
Fleischmann et al. Swiss Prot. Database Accession No. Q57243, Nov. 1, 1997.*
Kunst et al; SPTREM BL Database Accession No: 031716, Jan. 1, 1998.*
Anderson et al; Gen Seq. Database Accession No: AAR98196, Aug. 16, 1996.*
Paiichi Sei Yakukk.; Gen Seq Database Accession No: AAP51212, Jan. 8, 1992.*
Blahner et al. PIR Database Accession No: D64819, Sep. 12, 1997.*
Jeanine Alligent et al., Characterization of a new staphylococcal gene, vgaB, encoding a putative ABC transporter conferring resistance to streptogramin A and related compounds, GENE, Apr. 29, 1997, pp. 133–138.

* cited by examiner

*Primary Examiner*—Patricia A. Duffy
(74) *Attorney, Agent, or Firm*—Pillsbury Winthrop LLP

(57) ABSTRACT

The present invention concerns the treatment and diagnosis of Staphylococcal infections, particularly those of *Staphylococcus aureus*, and provides a protein, epitopes of same, and antibodies and other binding and neutralizing agents specific against same.

17 Claims, No Drawings

SEQUENCE LISTING

<160> NUMBER OF SEQ ID NOS: 18

<210> SEQ ID NO 1
<211> LENGTH: 1602
<212> TYPE: DNA
<213> ORGANISM: Staphylococcus aureus
<220> FEATURE:
<221> NAME/KEY: CDS
<222> LOCATION: (1)..(1602)

<400> SEQUENCE: 1

| | | | | | | | | | | | | | | | | |
|---|---|---|---|---|---|---|---|---|---|---|---|---|---|---|---|---|
| atg | tta | caa | gta | act | gat | gtg | agt | tta | cgt | ttt | gga | gat | cgt | aaa | cta | 48 |
| Met | Leu | Gln | Val | Thr | Asp | Val | Ser | Leu | Arg | Phe | Gly | Asp | Arg | Lys | Leu | |
| 1 | | | | 5 | | | | | 10 | | | | | 15 | | |
| ttt | gaa | gat | gta | aat | att | aaa | ttt | aca | gaa | ggt | aat | tgt | tat | gga | tta | 96 |
| Phe | Glu | Asp | Val | Asn | Ile | Lys | Phe | Thr | Glu | Gly | Asn | Cys | Tyr | Gly | Leu | |
| | | | 20 | | | | | 25 | | | | | 30 | | | |
| att | ggt | gcg | aat | ggt | gca | ggt | aaa | tca | aca | ttt | tta | aaa | ata | tta | tct | 144 |
| Ile | Gly | Ala | Asn | Gly | Ala | Gly | Lys | Ser | Thr | Phe | Leu | Lys | Ile | Leu | Ser | |
| | | 35 | | | | | 40 | | | | | 45 | | | | |
| ggt | gaa | tta | gat | tct | caa | aca | gga | cat | gtt | tca | tta | ggg | aaa | aat | gaa | 192 |
| Gly | Glu | Leu | Asp | Ser | Gln | Thr | Gly | His | Val | Ser | Leu | Gly | Lys | Asn | Glu | |
| 50 | | | | | 55 | | | | | 60 | | | | | | |
| cgt | cta | gct | gtt | tta | aaa | cag | gac | cac | tat | gct | tat | gaa | gat | gaa | cgc | 240 |
| Arg | Leu | Ala | Val | Leu | Lys | Gln | Asp | His | Tyr | Ala | Tyr | Glu | Asp | Glu | Arg | |
| 65 | | | | | 70 | | | | | 75 | | | | | 80 | |
| gtg | ctt | gat | gtt | gta | att | aaa | ggt | cac | gaa | cgt | ctt | tat | gag | gtt | atg | 288 |
| Val | Leu | Asp | Val | Val | Ile | Lys | Gly | His | Glu | Arg | Leu | Tyr | Glu | Val | Met | |
| | | | | 85 | | | | | 90 | | | | | 95 | | |
| aaa | gaa | aaa | gat | gaa | atc | tat | atg | aag | cca | gat | ttc | agt | gat | gaa | gat | 336 |
| Lys | Glu | Lys | Asp | Glu | Ile | Tyr | Met | Lys | Pro | Asp | Phe | Ser | Asp | Glu | Asp | |
| | | | 100 | | | | | 105 | | | | | 110 | | | |
| ggt | atc | cgt | gct | gct | gaa | ctt | gaa | ggt | gaa | ttt | gca | gaa | atg | aat | ggt | 384 |
| Gly | Ile | Arg | Ala | Ala | Glu | Leu | Glu | Gly | Glu | Phe | Ala | Glu | Met | Asn | Gly | |
| | | 115 | | | | | 120 | | | | | 125 | | | | |
| tgg | aat | gct | gaa | gct | gat | gct | gct | aac | ctt | tta | tct | ggt | tta | ggt | atc | 432 |
| Trp | Asn | Ala | Glu | Ala | Asp | Ala | Ala | Asn | Leu | Leu | Ser | Gly | Leu | Gly | Ile | |
| | 130 | | | | | 135 | | | | | 140 | | | | | |
| gat | cca | act | tta | cac | gat | aaa | aaa | atg | gct | gaa | tta | gaa | aac | aac | caa | 480 |
| Asp | Pro | Thr | Leu | His | Asp | Lys | Lys | Met | Ala | Glu | Leu | Glu | Asn | Asn | Gln | |
| 145 | | | | | 150 | | | | | 155 | | | | | 160 | |
| aaa | att | aaa | gta | tta | tta | gcg | caa | agt | tta | ttc | ggt | gaa | cca | gac | gta | 528 |
| Lys | Ile | Lys | Val | Leu | Leu | Ala | Gln | Ser | Leu | Phe | Gly | Glu | Pro | Asp | Val | |
| | | | | 165 | | | | | 170 | | | | | 175 | | |
| cta | tta | ctg | gat | gag | cct | act | aac | ggt | ctg | gat | att | cca | gca | atc | agt | 576 |
| Leu | Leu | Leu | Asp | Glu | Pro | Thr | Asn | Gly | Leu | Asp | Ile | Pro | Ala | Ile | Ser | |
| | | | | 180 | | | | | 185 | | | | | 190 | | |
| tgg | tta | gaa | gat | ttc | tta | att | aac | ttt | gat | aat | act | gtt | atc | gta | gta | 624 |
| Trp | Leu | Glu | Asp | Phe | Leu | Ile | Asn | Phe | Asp | Asn | Thr | Val | Ile | Val | Val | |
| | | | 195 | | | | | 200 | | | | | 205 | | | |
| tca | cat | gac | cgc | cat | ttc | tta | aat | aat | gta | tgt | act | cat | atc | gct | gat | 672 |
| Ser | His | Asp | Arg | His | Phe | Leu | Asn | Asn | Val | Cys | Thr | His | Ile | Ala | Asp | |
| | | 210 | | | | | 215 | | | | | 220 | | | | |
| tta | gac | ttt | ggt | aaa | att | aaa | gtt | tat | gtt | ggt | aac | tat | gat | ttt | tgg | 720 |
| Leu | Asp | Phe | Gly | Lys | Ile | Lys | Val | Tyr | Val | Gly | Asn | Tyr | Asp | Phe | Trp | |
| 225 | | | | | 230 | | | | | 235 | | | | | 240 | |
| tat | caa | tct | agt | cag | tta | gct | caa | aag | atg | gct | caa | gaa | caa | aac | aag | 768 |
| Tyr | Gln | Ser | Ser | Gln | Leu | Ala | Gln | Lys | Met | Ala | Gln | Glu | Gln | Asn | Lys | |
| | | | | 245 | | | | | 250 | | | | | 255 | | |

| | | | | | | | | | | | | | | | |
|---|---|---|---|---|---|---|---|---|---|---|---|---|---|---|---|
| aag | aga | aga | gaa | aaa | atg | aaa | gag | tta | caa | gac | ttt | att | gct | cgt | ttc | 816 |
| Lys | Arg | Arg | Glu | Lys | Met | Lys | Glu | Leu | Gln | Asp | Phe | Ile | Ala | Arg | Phe | |
| | | 260 | | | | | 265 | | | | | 270 | | | | |
| tca | gct | aac | gct | tct | aaa | tct | aaa | caa | gca | aca | agt | cgt | aaa | aaa | caa | 864 |
| Ser | Ala | Asn | Ala | Ser | Lys | Ser | Lys | Gln | Ala | Thr | Ser | Arg | Lys | Lys | Gln | |
| | 275 | | | | | 280 | | | | | 285 | | | | | |
| ctt | gag | aaa | att | gaa | tta | gat | gat | att | caa | cca | tca | tca | aga | aga | tat | 912 |
| Leu | Glu | Lys | Ile | Glu | Leu | Asp | Asp | Ile | Gln | Pro | Ser | Ser | Arg | Arg | Tyr | |
| 290 | | | | | 295 | | | | | 300 | | | | | | |
| cct | ttc | gtt | aaa | ttc | acg | cct | gag | cgt | gag | att | ggt | aac | gac | tta | tta | 960 |
| Pro | Phe | Val | Lys | Phe | Thr | Pro | Glu | Arg | Glu | Ile | Gly | Asn | Asp | Leu | Leu | |
| 305 | | | | 310 | | | | | 315 | | | | | 320 | | |
| atc | gtt | caa | aat | ctt | tct | aaa | aca | att | gac | ggc | gaa | aaa | gta | tta | gat | 1008 |
| Ile | Val | Gln | Asn | Leu | Ser | Lys | Thr | Ile | Asp | Gly | Glu | Lys | Val | Leu | Asp | |
| | | | 325 | | | | | 330 | | | | | 335 | | | |
| aat | gta | tca | ttc | aca | atg | aat | cca | aat | gat | aaa | gcg | att | tta | att | gga | 1056 |
| Asn | Val | Ser | Phe | Thr | Met | Asn | Pro | Asn | Asp | Lys | Ala | Ile | Leu | Ile | Gly | |
| | | 340 | | | | | 345 | | | | | 350 | | | | |
| gat | agt | gaa | att | gca | aaa | aca | aca | tta | ctt | aaa | ata | tta | gct | ggc | gaa | 1104 |
| Asp | Ser | Glu | Ile | Ala | Lys | Thr | Thr | Leu | Leu | Lys | Ile | Leu | Ala | Gly | Glu | |
| | 355 | | | | | 360 | | | | | 365 | | | | | |
| atg | gaa | cca | gac | gaa | ggt | tca | ttt | aaa | tgg | ggt | gtt | act | aca | tca | tta | 1152 |
| Met | Glu | Pro | Asp | Glu | Gly | Ser | Phe | Lys | Trp | Gly | Val | Thr | Thr | Ser | Leu | |
| 370 | | | | | 375 | | | | | 380 | | | | | | |
| agt | tac | ttc | cct | aaa | gat | aac | tca | gag | ttc | ttt | gag | ggt | gta | aat | atg | 1200 |
| Ser | Tyr | Phe | Pro | Lys | Asp | Asn | Ser | Glu | Phe | Phe | Glu | Gly | Val | Asn | Met | |
| 385 | | | | 390 | | | | | 395 | | | | | 400 | | |
| aat | ctc | gtt | gat | tgg | tta | aga | caa | tat | gct | cct | gaa | gat | gaa | caa | aca | 1248 |
| Asn | Leu | Val | Asp | Trp | Leu | Arg | Gln | Tyr | Ala | Pro | Glu | Asp | Glu | Gln | Thr | |
| | | | 405 | | | | | 410 | | | | | 415 | | | |
| gaa | aca | ttt | tta | cgt | ggt | ttc | tta | ggt | cgt | atg | tta | ttt | agt | ggt | gaa | 1296 |
| Glu | Thr | Phe | Leu | Arg | Gly | Phe | Leu | Gly | Arg | Met | Leu | Phe | Ser | Gly | Glu | |
| | | 420 | | | | | 425 | | | | | 430 | | | | |
| gaa | gtt | aag | aaa | aaa | gct | agt | gtg | ctt | tca | ggt | gga | gaa | aaa | gta | cgt | 1344 |
| Glu | Val | Lys | Lys | Lys | Ala | Ser | Val | Leu | Ser | Gly | Gly | Glu | Lys | Val | Arg | |
| | 435 | | | | | 440 | | | | | 445 | | | | | |
| tgt | atg | tta | agt | aaa | atg | atg | tta | tca | agt | gcg | aat | gta | ctt | tta | ctt | 1392 |
| Cys | Met | Leu | Ser | Lys | Met | Met | Leu | Ser | Ser | Ala | Asn | Val | Leu | Leu | Leu | |
| 450 | | | | | 455 | | | | | 460 | | | | | | |
| gac | gaa | cct | act | aac | cac | tta | gac | tta | gaa | agt | att | act | gct | gtc | aat | 1440 |
| Asp | Glu | Pro | Thr | Asn | His | Leu | Asp | Leu | Glu | Ser | Ile | Thr | Ala | Val | Asn | |
| 465 | | | | 470 | | | | | 475 | | | | | 480 | | |
| gat | ggt | ctt | aaa | tca | ttt | aaa | ggt | tct | atc | atc | ttt | act | tct | tat | gac | 1488 |
| Asp | Gly | Leu | Lys | Ser | Phe | Lys | Gly | Ser | Ile | Ile | Phe | Thr | Ser | Tyr | Asp | |
| | | | 485 | | | | | 490 | | | | | 495 | | | |
| ttc | gaa | ttt | atc | aac | acg | att | gca | aac | cgt | gtt | atc | gat | tta | aat | aaa | 1536 |
| Phe | Glu | Phe | Ile | Asn | Thr | Ile | Ala | Asn | Arg | Val | Ile | Asp | Leu | Asn | Lys | |
| | | 500 | | | | | 505 | | | | | 510 | | | | |
| caa | ggc | ggc | gtt | tca | aaa | gaa | att | cca | tat | gaa | gaa | tac | ttg | caa | gaa | 1584 |
| Gln | Gly | Gly | Val | Ser | Lys | Glu | Ile | Pro | Tyr | Glu | Glu | Tyr | Leu | Gln | Glu | |
| | 515 | | | | | 520 | | | | | 525 | | | | | |
| atc | ggc | gtt | tta | aaa | taa | | | | | | | | | | | 1602 |
| Ile | Gly | Val | Leu | Lys | | | | | | | | | | | | |
| | 530 | | | | | | | | | | | | | | | |

<210> SEQ ID NO 2
<211> LENGTH: 533
<212> TYPE: PRT
<213> ORGANISM: Staphylococcus aureus

<400> SEQUENCE: 2

-continued

```
Met Leu Gln Val Thr Asp Val Ser Leu Arg Phe Gly Asp Arg Lys Leu
 1               5                  10                  15

Phe Glu Asp Val Asn Ile Lys Phe Thr Glu Gly Asn Cys Tyr Gly Leu
                20                  25                  30

Ile Gly Ala Asn Gly Ala Gly Lys Ser Thr Phe Leu Lys Ile Leu Ser
            35                  40                  45

Gly Glu Leu Asp Ser Gln Thr Gly His Val Ser Leu Gly Lys Asn Glu
        50                  55                  60

Arg Leu Ala Val Leu Lys Gln Asp His Tyr Ala Tyr Glu Asp Glu Arg
 65                  70                  75                  80

Val Leu Asp Val Val Ile Lys Gly His Glu Arg Leu Tyr Glu Val Met
                85                  90                  95

Lys Glu Lys Asp Glu Ile Tyr Met Lys Pro Asp Phe Ser Asp Glu Asp
                100                 105                 110

Gly Ile Arg Ala Ala Glu Leu Glu Gly Glu Phe Ala Glu Met Asn Gly
            115                 120                 125

Trp Asn Ala Glu Ala Asp Ala Ala Asn Leu Leu Ser Gly Leu Gly Ile
        130                 135                 140

Asp Pro Thr Leu His Asp Lys Lys Met Ala Glu Leu Glu Asn Asn Gln
145                 150                 155                 160

Lys Ile Lys Val Leu Leu Ala Gln Ser Leu Phe Gly Glu Pro Asp Val
                165                 170                 175

Leu Leu Leu Asp Glu Pro Thr Asn Gly Leu Asp Ile Pro Ala Ile Ser
            180                 185                 190

Trp Leu Glu Asp Phe Leu Ile Asn Phe Asp Asn Thr Val Ile Val Val
        195                 200                 205

Ser His Asp Arg His Phe Leu Asn Asn Val Cys Thr His Ile Ala Asp
210                 215                 220

Leu Asp Phe Gly Lys Ile Lys Val Tyr Val Gly Asn Tyr Asp Phe Trp
225                 230                 235                 240

Tyr Gln Ser Ser Gln Leu Ala Gln Lys Met Ala Gln Glu Gln Asn Lys
                245                 250                 255

Lys Arg Arg Glu Lys Met Lys Glu Leu Gln Asp Phe Ile Ala Arg Phe
            260                 265                 270

Ser Ala Asn Ala Ser Lys Ser Lys Gln Ala Thr Ser Arg Lys Lys Gln
        275                 280                 285

Leu Glu Lys Ile Glu Leu Asp Asp Ile Gln Pro Ser Ser Arg Arg Tyr
    290                 295                 300

Pro Phe Val Lys Phe Thr Pro Glu Arg Glu Ile Gly Asn Asp Leu Leu
305                 310                 315                 320

Ile Val Gln Asn Leu Ser Lys Thr Ile Asp Gly Glu Lys Val Leu Asp
                325                 330                 335

Asn Val Ser Phe Thr Met Asn Pro Asn Asp Lys Ala Ile Leu Ile Gly
            340                 345                 350

Asp Ser Glu Ile Ala Lys Thr Thr Leu Leu Lys Ile Leu Ala Gly Glu
        355                 360                 365

Met Glu Pro Asp Glu Gly Ser Phe Lys Trp Gly Val Thr Thr Ser Leu
    370                 375                 380

Ser Tyr Phe Pro Lys Asp Asn Ser Glu Phe Phe Glu Gly Val Asn Met
385                 390                 395                 400

Asn Leu Val Asp Trp Leu Arg Gln Tyr Ala Pro Glu Asp Glu Gln Thr
                405                 410                 415
```

```
Glu Thr Phe Leu Arg Gly Phe Leu Gly Arg Met Leu Phe Ser Gly Glu
        420                 425                 430

Glu Val Lys Lys Ala Ser Val Leu Ser Gly Gly Glu Lys Val Arg
        435                 440                 445

Cys Met Leu Ser Lys Met Met Leu Ser Ser Ala Asn Val Leu Leu Leu
        450                 455                 460

Asp Glu Pro Thr Asn His Leu Asp Leu Glu Ser Ile Thr Ala Val Asn
465                 470                 475                 480

Asp Gly Leu Lys Ser Phe Lys Gly Ser Ile Ile Phe Thr Ser Tyr Asp
                485                 490                 495

Phe Glu Phe Ile Asn Thr Ile Ala Asn Arg Val Ile Asp Leu Asn Lys
                500                 505                 510

Gln Gly Val Ser Lys Glu Ile Pro Tyr Glu Glu Tyr Leu Gln Glu
        515                 520                 525

Ile Gly Val Leu Lys
        530
```

<210> SEQ ID NO 3
<211> LENGTH: 4
<212> TYPE: PRT
<213> ORGANISM: Staphylococcus aureus

<400> SEQUENCE: 3

Gly Asn Tyr Asp
1

<210> SEQ ID NO 4
<211> LENGTH: 5
<212> TYPE: PRT
<213> ORGANISM: Staphylococcus aureus

<400> SEQUENCE: 4

Arg Arg Tyr Pro Phe
1               5

<210> SEQ ID NO 5
<211> LENGTH: 4
<212> TYPE: PRT
<213> ORGANISM: Staphylococcus aureus

<400> SEQUENCE: 5

Arg Gly Phe Leu
1

<210> SEQ ID NO 6
<211> LENGTH: 15
<212> TYPE: PRT
<213> ORGANISM: Staphylococcus aureus

<400> SEQUENCE: 6

Lys Ile Lys Val Tyr Val Gly Asn Tyr Asp Phe Trp Tyr Gln Ser
1               5                   10                  15

<210> SEQ ID NO 7
<211> LENGTH: 15
<212> TYPE: PRT
<213> ORGANISM: Staphylococcus aureus

<400> SEQUENCE: 7

Asp Ile Gln Pro Ser Ser Arg Arg Tyr Pro Phe Val Lys Phe Thr
1               5                   10                  15

```
<210> SEQ ID NO 8
<211> LENGTH: 15
<212> TYPE: PRT
<213> ORGANISM: Staphylococcus aureus

<400> SEQUENCE: 8

Thr Glu Thr Phe Leu Arg Gly Phe Leu Gly Arg Met Leu Phe Ser
 1               5                  10                  15

<210> SEQ ID NO 9
<211> LENGTH: 6
<212> TYPE: PRT
<213> ORGANISM: Staphylococcus aureus

<400> SEQUENCE: 9

Asp Arg His Phe Leu Asn
 1               5

<210> SEQ ID NO 10
<211> LENGTH: 6
<212> TYPE: PRT
<213> ORGANISM: Staphylococcus aureus

<400> SEQUENCE: 10

Lys Thr Thr Leu Leu Lys
 1               5

<210> SEQ ID NO 11
<211> LENGTH: 7
<212> TYPE: PRT
<213> ORGANISM: Staphylococcus aureus

<400> SEQUENCE: 11

Gly Val Thr Thr Ser Leu Ser
 1               5

<210> SEQ ID NO 12
<211> LENGTH: 5
<212> TYPE: PRT
<213> ORGANISM: Staphylococcus aureus

<400> SEQUENCE: 12

Val Asp Trp Leu Arg
 1               5

<210> SEQ ID NO 13
<211> LENGTH: 15
<212> TYPE: PRT
<213> ORGANISM: Staphylococcus aureus

<400> SEQUENCE: 13

Glu Pro Asp Val Leu Leu Leu Asp Glu Pro Thr Asn Gly Leu Asp
 1               5                  10                  15

<210> SEQ ID NO 14
<211> LENGTH: 15
<212> TYPE: PRT
<213> ORGANISM: Staphylococcus aureus

<400> SEQUENCE: 14

Leu Ile Gly Asp Ser Glu Ile Ala Lys Thr Thr Leu Leu Lys Ile
 1               5                  10                  15

<210> SEQ ID NO 15
```

```
<211> LENGTH: 21
<212> TYPE: DNA
<213> ORGANISM: Staphylococcus aureus

<400> SEQUENCE: 15
ttttaaaacg ccgatttctt g                                              21

<210> SEQ ID NO 16
<211> LENGTH: 19
<212> TYPE: DNA
<213> ORGANISM: Staphylococcus aureus

<400> SEQUENCE: 16
atgttacaag taactgatg                                                 19

<210> SEQ ID NO 17
<211> LENGTH: 9
<212> TYPE: PRT
<213> ORGANISM: Staphylococcus aureus

<400> SEQUENCE: 17

Gly Ala Asn Gly Ala Gly Lys Ser Thr
 1               5

<210> SEQ ID NO 18
<211> LENGTH: 12
<212> TYPE: PRT
<213> ORGANISM: Staphylococcus aureus

<400> SEQUENCE: 18

Gly Ala Asn Gly Ala Gly Lys Ser Thr Phe Leu Lys
 1               5                  10
```

STAPHYLOCOCCAL ABC TRANSPORTER PROTEIN

CROSS REFERENCE TO RELATED APPLICATION

This is a Continuation of International Application No. PCT/GB99/00939, filed Mar. 25, 1999.

The present invention concerns the treatment and diagnosis of Staphylococcal infections, particularly those of *Staphylococcus aureus*, and provides a protein, epitopes of same, and antibodies and other binding and neutralising agents specific against same.

Multiple drug resistance (MDR) is an increasing problem amongst gram-positive bacteria (Banergee, S. N. et al. 1991, Am. J. Med. 91: 865–895; Shaberg, D. R. et al., 1991, Am. J. Med. suppl., 88: 72–75; Gaynes, R. P. et al., 1994, Infect. Dis. Clin. Pract., 6: 452–455), particularly in hospitals. In particular, methicillin-resistant *Staphylococcus aureus* (MRSA) and coagulase-negative staphylococci (CNS), particularly methicillin-resistant CNS, prove problematic, being resistant to all penicillins and cephalosporins. Resistance to other agents such as quinolones is widespread (Malabarta, A. et al., 1997, Eur. J. Med. Chem., 32: 459–478; Lewis, K., 1994, TIBS, 19: 119–123; Traub, W. H. et al., 1996, Chemotherapy, 42: 118–132). Treatment is typically effected using vancomycin or teicoplanin. However, resistance to these agents is spreading and so new therapies are needed.

WO 98/01154 discloses the use of bacterial and fungal ABC transporter proteins and neutralising agents specific against same in methods of treatment and diagnosis of the human or animal body. Enterococcal ABC transporter proteins having apparent molecular weights of 97 and 54 kDa are identified as being therapeutically useful, and various epitopes are also identified. Staphylococcal homologues of the IstA and IstB proteins of *Bacillus thuringiensis* (Menou et al., 1990, J. of Bacteriology, 173: 6689–6696) are also identified, the homologues having apparent molecular weights of 69 and 37 KDA and being immunodominant conserved antigens. Also identified are epitopes of same.

A Staphylococcal ABC transporter protein having an apparent molecular weight of 67 KDA has now been successfully isolated and purified by the present inventor from an epidemic MRSA strain, and has the coding sequence of SEQ ID NO: 1 and the amino acid sequence of SEQ ID NO: 2. These sequences are partially identified by the *S. aureus* NCTC 8325 genome sequencing project as contig 1184, contig 1177 and contig 1158 containing amino-terminal sequence data. This protein has not previously been suggested to be an ABC transporter protein, and no diagnostic or therapeutic uses have previously been suggested for it. The protein has a calculated true molecular weight of 60.1 kDa, although post-translational modifications result in its being identified in experiments as having an apparent molecular weight of 67 kDa.

The role of the protein is neither suggested nor disclosed by the IstA and IstB homologues of WO 98/01154 since they have different sequences and different molecular weights. Additionally, the samples from which the IstA and IstB homologues were isolated were peritoneal dialysates rather than the blood and wound cultures used for the present invention (below), and such a purification method could not have led to the present invention since the previously used dialysis step caused a change in the relative proportions of antibody in the dialysate when compared to serum. Similarly, other known prior art does not suggest the role of the protein, nor does it suggest it to have a diagnostic or therapeutic use.

Thus according to the present invention there is provided a Staphylococcal ABC transporter protein having the sequence of SEQ ID NO: 2 or a partially modified form thereof or an immunogenic fragment thereof for use in a method of treatment or diagnosis of the human or animal body.

Immunogenic fragments of the protein include any fragment of the protein which elicit an immune response, and include epitopes (i.e. peptides carrying epitopes). Similarly, analogues (mimotopes) of epitopes may be readily created, the mimotopes having different sequences but displaying the same epitope and thus the term "immunogenic fragments" also encompasses immunogenic analogues of the fragments e.g. mimotopes. Epitopes may be readily determined and mimotopes readily designed (Geysen, H. M. et al., 1987, Journal of Immunological Methods, 102: 259–274; Geysen, H. M. et al.,1988, J. Mol. Recognit., 1(1):32–41; Jung, G. and Beck-Sickinger, A. G., 1992, Angew. Chem. Int. Ed. Eng., 31: 367–486).

The scope of the present invention does not extend to other non-Staphylococcal ABC transporter proteins, such as those of WO 98/01154. However, the invention does extend to encompass forms of the protein which have been insubstantially modified (i.e. which have been partially modified), particularly forms of the protein which display the same immunogenic properties as the protein itself.

By "partial modification" and "partially modified" is meant, with reference to amino acid sequences, a partially modified form of the molecule which retains substantially the properties of the molecule from which it is derived, although it may of course have additional functionality. Partial modification may, for example, be by way of addition, deletion or substitution of amino acid residues. Substitutions may be conserved substitutions. Hence the partially modified molecule may be a homologue of the molecules from which it was derived. It may, for example, have at least 70% homology with the molecule from which it was derived. It may for example have at least 80, 90 or 95% homology with the molecule from which it was derived. An example of a homologue is an allelic mutant. Similarly nucleotide sequences encoding the molecule or amino acid sequences may be partially modified to code for any such modifications to an amino acid sequence or molecule. Nucleotide sequences may also of course be modified such that they still code for the same amino acid residues but have a different nucleotide sequence.

The Staphylococcus may be *S. aureus* or it may for example be a coagulase-negative Staphylococcus, *S. epidermidis, S. haemolyticus, S. hyicus* or *S. saprophyticus*.

An immunogenic fragment may comprise an ATP binding site or a part thereof. Peptides carrying (i.e. displaying) a number of epitopes of the ABC transporter protein have also been identified (below) and thus an immunogenic fragment of the protein may comprise the sequence of SEQ ID NO: 3,4,5,9,10,11 or 12. The epitopes of SEQ ID NOs: 3,4 and 5 are displayed by peptides having the sequences of SEQ ID NOs: 6,7 and 8 respectively, and thus an immunogenic fragment may comprise the sequence of SEQ ID NO: 6,7 or 8. In particular, experiments have shown that peptides having SEQ ID NOs: 6 and 7 which display epitopes having SEQ ID NOs: 3 and 4 are of particular therapeutic use. Peptides having the sequences of SEQ ID NOs: 13 and 14 have also been found to carry epitopes, antibody against which is therapeutic in an animal model (see experiments below) and thus an immunogenic fragment may have the formula of SEQ ID NO: 13 or 14. An additional epitope having the sequence of SEQ ID NO: 17 has also been found, and a peptide having the sequence of SEQ ID NO: 18 carrying same elicits the generation of polyclonal antisera specific against the 67 kDa antigen. Thus an immunogenic fragment may have the sequence of either one of SEQ ID NOs: 17 or 18.

The Staphylococcal ABC transporter protein, displaying epitopes including those described above, therefore provides a therapeutic and diagnostic opportunity—the protein and immunogenic fragments thereof may be used in therapy, both prophylactically (e.g. as immunostimulants such as vaccines) and for treatment of a Staphylococcal infection.

Binding agents and neutralising agents (such as antibodies) specific against the ABC transporter protein, immunogenic fragments thereof or partially modified forms thereof may also be used both diagnostically and therapeutically. Binding agents have a target to which they are specific, and in the case of a binding agent being an antibody, the target is an antigen. An example of a therapeutic medicament is antibody specific against the ABC transporter protein, and this may be employed in immunotherapy, for example passive immunotherapy. Antibodies, their manufacture and use are well known (Harlow, E. and Lane, D., "Antibodies—A Laboratory Manual", Cold Spring Harbor Laboratory, Cold Spring Harbor Press, New York, 1988; Harlow, E. and Lane, D., "Using Antibodies: A Laboratory Manual", Cold Spring Harbor Laboratory Press, New York, 1998) and so antibodies and antigen binding fragments thereof will be readily apparent to one skilled in the art.

The nucleotide sequence of the protein or immunogenic fragment may also provide the basis for therapeutic applications. For example a nucleotide sequence encoding the protein or immunogenic fragment thereof may be used in the manufacture of a DNA vaccine (Montgomery, D. L. et al., 1997, Pharmacol. Ther., 74(2): 195–205; Donnelly, J. J. et al., 1997, Annu. Rev. Immunol., 15: 617–648; Manickan, E. et al., 1997, Crit. Rev. Immunol., 17(2): 139–154). Other neutralising agents such as ribozymes and antisense oligonucleotides will be readily apparent to one skilled in the art.

Thus the present invention also provides the use of the Staphylococcal ABC transporter protein, immunogenic fragment of same, binding agents and neutralising agents specific against same in a method of manufacture of a medicament for treating Staphylococcal infections. Also provided is a method of manufacture of a medicament for treating Staphylococcal infections, characterised in the use of same. Also provided is a method of treatment of the human or animal body comprising the use of same. The dosage of a medicament may be readily determined by standard dose-response experiments. Medicaments may additionally comprise a pharmaceutically acceptable carrier, diluent or excipient (Remington's Pharmaceutical Sciences and US Pharmacopeia, 1984, Mack Publishing Company, Easton, Pa., USA).

As discussed above, the ABC transporter protein, immunogenic fragments of same, binding agents and neutralising agents specific against same may also be used diagnostically, and so the present invention provides for their use in the manufacture of a diagnostic test kit for Staphylococci, particularly for Staphylococcal infections. Also provided is their use in a diagnostic test method for Staphylococci.

Also provided according to the present invention is a diagnostic test method for Staphylococcal infection, comprising the steps of:

i) reacting an ABC transporter protein or immunogenic fragment thereof according to the present invention with a sample;

ii) detecting an antibody-antigen binding reaction; and iii) correlating detection of the antibody-antigen binding reaction with the presence of Staphylococci.

Also provided according to the present invention is a diagnostic test method for Staphylococcal infection, comprising the steps of:

i) reacting an antibody or other binding agent specific against an ABC transporter protein according to the present invention with a sample;

ii) detecting a binding agent-target binding reaction; and iii) correlating detection of the binding agent-target binding reaction with the presence of Staphylococci.

Samples may be of patient plasma or a fraction thereof e.g. sera or antisera. The diagnostic test method may be for Staphylococcal infection of a patient, the sample being a patient sample and the correlation determining Staphylococcal infection of the patient.

Also provided according to the present invention is a diagnostic test kit for performing a diagnostic test method according to the present invention. The diagnostic test kit may include instructions for performing a diagnostic test using the kit.

Also provided according to the present invention is a method of treatment or diagnosis of Staphylococcal infection comprising the use of a Staphylococcal ABC transporter protein, immunogenic fragment thereof, binding agent or neutralising agent according to the present invention.

The invention will be further apparent from the following description which show, by way of example only, diagnosis and treatment of Staphylococcal infections.

Experimental

Experiments were performed using MRSA sera from blood and wound cultures of various groups of patients. Antigenic extracts were prepared from each group and screened against patient antisera. This identified a 67 kDa antigen, and an expression library created from an epidemic MRSA strain was then screened, allowing the identification of the protein. Epitope mapping then identified antigenic regions of the protein and further experiments identified epitopes and peptides carrying same with therapeutic potential.

Immunoblotting
Bacterial Strains

An epidemic MRSA (EMRSA) strain was obtained from the Clinical Microbiology Laboratory at the Manchester Royal Infirmary (MRI). Strain referred to as EMRSA (VSRS) as it was sensitive to vancomycin and rifampicin. A separate isolate of the same clone was obtained from a patient where rifampicin resistance had been induced in vivo by rifampicin administration (VSRR).

Groups of Sera

Group 1 Infected patients, either sputum or wound, requiring treatment with systemic vancomycin and rifampicin (n=3). Isolates rifampicin sensitive throughout.

Group 2 Blood culture positive, requiring treatment with systemic vancomycin and rifampicin (n=3). Isolates rifampicin sensitive throughout.

Group 3 Colonized leg ulcer in diabetic patient with rifampicin resistant clone (n=3). No systemic therapy.

Group 4 Septicaemia, blood culture positive, treated by vancomycin and rifampicin (n=3). Strain became resistant to rifampicin during treatment.

Preparation of Vancomycin Resistant EMRSA

Single colonies of the above (VRRS and VSRR) were inoculated in a 10 ml nutrient broth number 2 (Oxoid, UK) with vancomycin at 1 μg/ml and incubated at 37° C. with shaking. When the broth became turbid, four drops (120 μl), were used to inoculate another 10 ml broth with 2 μg/ml vancomycin. When this broth became turbid, 120 μl of the culture were used to inoculate another broth with 3 μg/ml vancomycin. This was repeated with gradually increasing concentration of vancomycin 4, 5, 6, 7, 8 μg/ml and so on until it reached to 22 μg/ml for EMRSA 15 and to 16 μg/ml for the rifampicin-resistant EMRSA. The new clones were called VSRR and VRRR respectively.

A culture with the high resistance to vancomycin was used to inoculate four 1 liter flasks each containing 500 ml of nutrient broth number 2. This was 30 μg/ml for the rifampicin sensitive strain and 20 μg/ml for the rifampicin resistant isolate.

Collection of Broth Samples for Vancomycin Assay

After adding vancomycin into the broth using a sterile 5 ml pipette, the flask was shaken gently. Before inoculating the flask with the test bacteria a sample of the broth (1 ml) was taken using a fresh sterile pipette. The sample was sent into the Clinical Microbiology Laboratory for vancomycin assay.

The flasks were incubated at 37° C. with shaking (200 rpm) until the broth became turbid. Before harvesting the cells, a sample (2 ml) of the broth was obtained, using a sterile pipette in the safety cabinet. The sample was centrifuged at 13,000 rpm for 10 minutes. The precipitant was discarded in Hibitane, and the supernatant was filtered using Millipore 0.22 μm filter and then was sent for vancomycin assay. The value for the rifampicin sensitive strain at the start of the inoculation was 27.1 μg/ml and at the end 8.1 μg/ml. The corresponding values for the rifampicin resistant clone were 20.7 μg/ml and 7 μg/ml.

Harvesting Cells

The following steps were done in the safety cabinet. A blood agar purity plate was made from each culture at the time of harvesting to make sure the cultures had not become contaminated. Cells were harvested after incubation by centrifugation at 3500 rpm for 15 minutes. The supernatants were discarded in Hibitane. The deposits were washed twice in sterile saline, with centrifugation at 3500 rpm for 15 minutes after each wash.

Lysis of the Cells Using the Bio X-press Cell Disintegrator

Harvested cells were pipetted into the empty cylinder of the assembled Bio X-Press disintegrator (LKB Instruments, Bromma, Sweden) using a disposable plastic pipette, the second plunger was placed into the cylinder with the flat side facing downwards. The piston was pushed to its place until slight resistance was felt. The assembly was then covered with a plastic wrap and turned on its side with the cylinder containing the cells in an elevated level and left overnight at −20° C. The hand operated hydraulic pump was attached to the hydraulic press with the threaded collar finger tight. The plastic cover was removed from the frozen disintegrator which was then placed in an upright position on the press with the piston of the disintegrator towards the top of the press. The plastic support was placed on top of the disintegrator's piston with the support located centrally on the piston, the handle slowly pumped until the plastic support rose to the top of the press and the pumping continued until a number of "cracks" were heard whilst pumping, with the needle on the pressure gauge not entering the red area, the pressure was released by turning the lever on the pump, once the piston had travelled the full distance.

The disintegrator was disassembled and using a spatula the crushed cells were scooped into a sterile container. The cells were spun at 3500 rpm for 10 minutes, the supernatant was removed and the pellet discarded. The supernatant was later used at a suitable concentration in sodium dodecyl sulphate polyacrylamide gel electrophoresis (SDS-PAGE).

Sodium Dodecyl Sulphate Polyacrylamide Gel Electrophoresis (SDS-PAGE)

Preparation of Equipment and Gels for SDS-PAGE

For using this technique the following equipments were used to make two gels: 4 side clamps, 2 short glass plates, 2 long glass plates, 4 plate separators, 2 rubber bases and a base clamp.

To prepare each gel a pair of glass plates (short and long) were clamped together at their sides. A space between the two plates was created by plate separators. The plates were placed on a rubber base seal and secured into a base clamp. Distilled water was poured between the plates to a level just above the arrows on the side clamps. The water level was marked with felt tip pen and left for a few minutes to make sure there were no leaks. The water was then tipped out.

A mark was made 4 cm down from the top of the shorter glass plate and marked. The resolving gel mixture was poured into the equipment to that height. Using a plastic pipette a layer of distilled water was added to the top of gel mixture which was left to set for about 60 minutes at room temperature. When set, the layer of distilled water was poured out from the top of the resolving gel, and a 10 well comb was inserted between the two glass plates at an angle of 45°. About 5 mls of stacking gel mixture were added using a pipette, carefully avoiding the creation of bubbles, the comb was inserted and centred, and further gel mixture was added and overfilled the top of the plate, and left for 30 minutes to set. The gels can be used on the same day or stored in the cold room overnight after wrapping the tops of the resolving gel and the comb with a piece of plastic wrap.

To use the gel, the comb was gently removed, and the wells were washed out 3 times with electrophoresis buffer. Any electrophoresis buffer left in the bottom of the well was removed with a syringe and needle. The glass plates containing the gel were removed from the base clamp and clipped to the tank holder which was lowered into the electrophoresis tank.

Preparation and Loading of Specimens

The specimens were prepared in 1.5 ml eppendorf tubes. A total of 25 μl of each sample to be ran on the gel (diluted in distilled water according to the results of antigen titration) were mixed with 25 μl of cracking buffer. A total of 20 μl of the cracking buffer was also added to 20 μl of Rainbow (RTM) coloured protein molecular weight marker (Amersham International plc, Buckinghamshire).

The specimens and the marker in cracking buffer were boiled for 2–3 minutes in a suitable container. Using a Gilson pipette 25 μl of the marker were then carefully loaded to well one and 50 μl of each sample to the appropriate well.

Electrophoresis buffer was layered onto the samples with a plastic pipette, carefully not allowing one specimen to drift into the next. The remaining space between the glass plates was filled up with electrophoresis buffer, and the centre tank was filled until the buffer is approximately 2 mm below the top of the tank, and the cooling water was turned on. The lid of the tank was replaced and the apparatus was switched on at a constant current of 40–50 mA per gel, and the bubbles rising in the centre tank were checked.

The gels were allowed to run for 3 hours, or until the blue line was about 1 cm above the bottom of the plate.

After switching off the electrophoresis power and water, the holder containing glass plates was taken out of the tank and excess electrophoresis buffer was tipped off. The glass plates set was unclipped, and the glass plates were separated by gently levering with a plastic side-piece (plate separator). After removal of the stacking gel, the separating gel was removed for either silver staining or transblotting.

Silver Staining of SDS-PAGE Gels

Separated proteins in polyacrylamide (resolving) gels were stained with the Daiichi Silver Stain-II kit (Integrated Separation Systems, Japan). Gels which were used in the titration of antigen preparations, and those gels used to compare protein expression in organisms grown under differing incubation conditions were stained by this method using the manufacturers instructions.

Immunoblotting

In order to study the antibody response, the sera were blotted against the separated organisms proteins which had been transferred to a nitro-cellulose membrane after SDS-PAGE. Addition of anti-human IgG or anti-human IgM conjugate, followed by the appropriate substrate, made it possible to visualise those protein bands to which IgG or IgM antibodies present in the sera bound.

Transblotting

Materials needed for each gel are a plastic gel holder (consists of two halves), two pieces of scotchbrite, 4 pieces of blotting paper and a piece of nitrocellulose membrane.

A transfer tank was partially filled with the transblotting buffer and a handle side of the plastic holder placed in the tank. Two pieces of scotchbrite were lowered onto the holder using a rolling motion to avoid trapping air bubbles. Two pieces of filter paper were placed over the scotchbrite in the same way. A piece of nitrocellulose membrane (BioRad Laboratories, Hercules, Calif., USA) which had been cut to a size of 15×16.5 cm was laid on top and allowed to soak for 20 minutes.

After the electrophoresis power and water (of SDS-PAGE) were turned off, the holder containing the glass plates was taken out of the electrophoresis tank. One set of plates was unclipped and the glass plates were separated by levering with a plastic side-piece. After removing the stacking gel, the resolving gel was slid off the glass plate so as to remove the remainder of stacking gel. The resolving gel was placed on top of the soaked nitrocellulose membrane, and a further two pieces of blotting paper were placed on the gel. The other half of the plastic holder was clipped into place and the holder with its contents was lowered into the transblotting tank (Transphor Power Lid, Hoefer Scientific Instruments, San Francisco, USA). The lid of the tank was replaced and the cooling water was turned on. The apparatus was run at maximum power for 45 minutes.

When transblotting was complete the current was switched off and the cooling water was turned off. The holder was removed and unclipped and the gel and nitrocellulose membrane removed. The membrane was cut with a sharp scalpel to the size of the gel and left in 100 ml of 3% BSA (Sigma Chemical Co, St Louis, USA) at 4° C. overnight.

Antibody Probing, Conjugation and Staining Techniques

Both the top and the bottom of the nitrocellulose membrane were marked using a 10 well comb as a guide. The membrane was cut into strips using a scalpel and a ruler. The strips were placed in a strip box, and each strip was covered with 3.8 ml of 3% BSA (3% BSA in which the nitrocellulose has been stored overnight was used). A total volume of 200 $\mu$l of the serum to be immunoblotted was added for each strip, making a serum dilution of 1:20. The strips were incubated on a rotatory shaker for 2 hours at room temperature.

Using the washing solution the strips were washed 5 times for 6 minutes each time. Anti-human IgG or anti-human IgM alkaline phosphatase conjugate in a dilution of 1:1000 (diluted in 3% BSA) was added to the appropriate strips and shaken at room temperature for 1 hour. The strips were again washed 5 times as before. Meanwhile, NBT (nitro-blue tetrazolium) and BCIP (5 bromo4-chloro 3-indolyl phosphate) were prepared by adding 1 ml of DMF (n,n-dimethyl formamide) to 0.05 g of each of these powders. Just prior to use, a volume of 660 $\mu$l of NBT and 330 $\mu$l of BCIP were added to 100 ml of alkaline phosphatase substrate buffer. Five milliliters of this solution were added to each strip until well stained (approximately 5–15 minutes). The reaction was then stopped by washing the strips with distilled water, and they were placed on blotting paper to dry.

Preparation and Screening of a Genomic Expression Library of Methicillin Resistant *Staphylococcus aureus*

A genomic library was constructed in the expression/cloning vector lambda ZAP express, essentially as described by Young and Davies (1983, PNAS USA, 80: 1194–1198). Chromosomal DNA from a clinical isolate was partially digested by Sau3a and fragments in the size range of 2 to 9 kbp were inserted into the vector, resulting in the production of β galactosidase fusion proteins. Each library was screened with IgG antibody positive for the 67 kDa band of EMRSA (1 in 100 dilution) from a patient who had recovered from a blood culture positive septicaemia. Positive clones were detected using alkaline phosphatase conjugated goat anti-human immunoglobulin (IgG) (1 in 5,000) (Sigma, Poole, UK). Lysogens were prepared from positive clones in *Escherichia coli* Y1089 according to Huynh, Young and Davies (1985, DNA cloning vol 1, a practical approach, IRL Press Oxford, p 49–78, Ed. D. M. Glover). The epitope expressed by each of the positive clones was identified by antigen-selection as described by Lyon et al. (1986, PNAS USA, 83:2989–2993). For this, the serum was affinity purified by hybridising with positive recombinant lambda plaques. The bound antibody was then eluted with glycine buffer pH 2.8, and used to immunoblot lysates of the relevant bacteria.

DNA Sequencing

PCR with T3 and T7 forward and reverse primers was used to amplify insert DNA from sera positive clones. This was subcloned into the TA Cloning System (version 1.3, Invitrogen Corporation, Oxon, UK) prior to DNA sequencing using the dideoxy termination method (sequence version 2.0 kit; United States Biochemical, Cambridge, UK). Initial sequencing reactions were performed using sequencing universal primers, the remaining sequence being determined using a primer walking strategy by progressively synthesising sequencing primers to generate new sequence data.

Conclusions

Immunoblotting

Silver staining the antigenic extracts (VSRS, VRRS, VSRR and VRRR) produced the same pattern for all four. Immunoblotting identified antigenic bands varying in apparent molecular weight from 27 to 140 KDa (Tables 1 and 2). Patients produced an antibody against the 67 KDa antigen in all four groups. This was especially true if they have had a blood culture positive infection requiring treatment with vancomycin. In Group 4, sequential sera were also available from two patients and both showed an increased level of antibody to this antigen as the patient recovered. This antigen was present in all four antigenic extracts. IgG was present in the sera of the patients who survived a septicaemia due to the rifampicin resistant strain but not in the sera of the patients who recovered from a rifampicin sensitive septicaemia.

A 67 KDa antigen positive serum was then used to screen the expression library produced from the EMRSA. Two positive clones were obtained. Antigen selection demonstrated an epitope expressed by both clones which reacted with the conserved 67 KDa antigen of an EMRSA epidemic strain. Sequencing demonstrated a partial sequence in frame with the β galactosidase gene. The total insert size was 4.5 Kb. The derived amino acid sequence produced a protein with three ATP-binding domains and a sequence homologous to the group of protein which are ABC transporters (Fath and Kilter 1993. Microbiological Reviews 37, 995–1017). This was the C-terminal of the protein, starting at amino acid 133 of SEQ ID NO: 2. The sequence was searched in the *S. aureus* NCTC 8325 genome sequence project database and this produced matches with contigs 1184, 1177 and 1158 which had sequences partially overlapping the identified sequence. This in turn allowed the synthesis of PCR primers for the cloning of the full gene encoding the protein.

The full ABC transporter protein was obtained from purified EMRSA DNA using the PCR primers having SEQ ID NOs: 15 and 16 (forward and reverse primers respectively).

The complete gene was cloned into the pBAD vector via the pBAD-TA-TOPO cloning kit (Invitrogen) and expressed in *E. coli*. Following the expression, the protein was purified using affinity chromatography, providing the protein in its native conformation. A column was made with the Ni-NTA slur from Qiagen, which binds the His tag on the N-terminal end of the protein. The protein was eluted off the column with 250 mM imidazole with a final protein concentration of 1 mg/ml.

Polyclonal antiserum was prepared by injecting rabbits with the ABC transporter (0.5 mg/injection in full Freund's adjuvant repeated after 14 days and the fortnightly in incomplete Freund's adjuvant). The pre- and post-bleed sera (obtained at 28 28 days) were immunoblotted against the pressate derived from the EMRSA epidemic strain at a dilution of 1 in 100. This demonstrated seroconversion to antigens of apparent molecular weights of 67 and 33 kDa. This further confirmed the identity of the 67 kDa Staphylococcal antigen.

Epitope Mapping

A series of overlapping nonapeptides covering residues 135–533 of the derived amino acid sequence were synthesised on polythylene pins with reagents from an epitope scanning kit (Cambridge Research Biochemicals, Cambridge, United Kingdom) as described by Geysen, H. M. et al. (Journal of Immunological Methods, 102: 259–274). Peptide 1 consisted of residues 1 to 9, peptide 2 consisted of residues 2 to 10 etc. The reactivity of each peptide with patients' sera (1:200) was determined for IgG by ELISA. Data were expressed as A405 after 30 minutes of incubation. Sera from patients with EMRSA colonisation of a significant clinical site (chronic ambulatory dialysate post infection (n=2), infected amputation stump post infection (n=3) with negative blood cultures but still requiring systemic vancomycin therapy, septicaemia due to EMRSA successfully treated by vancomycin and rifampicin (post infection, n=4), fatal Septicaemia due to EMRSA (n=4)) and in patient hospital control sera (n=2) were examined.

Indirect ELISA

Three epitopes derived from the above were subsequently chosen (SEQ ID NOs: 3–5) and peptides 1–3 (SEQ ID NOs: 6–8) representing them were synthesised by a BT7400 multiple peptide synthesiser (Biotech Instruments, Luton, UK). These were used in the indirect ELISA.

Sera

Group A No evidence EMRSA colonisation or infection (n=12).
Group B Patients colonised by EMRSA at a clinically important site, chronic ambulatory dialysate (n=2) or amputation site (n=2) and requiring systemic vancomycin therapy for cure.
Group C Patients who survived a Septicaemia due to EMRSA treated by vancomycin (n=3).
Group D Patients who died from a septicaemia due to EMRSA (n=3).

By a simple adsorption of peptides to a microtitre plate the following procedure was performed for each peptide. The peptide was dissolved in 2 ml of 0.01 M phosphate buffer saline (PBS), pH 7.2 and diluted to a concentration of 10 µg/ml (1/100) in the same buffer.

Indirect ELISA was also performed with peptides 4 and 5 having the sequences of SEQ ID NOs: 13 and 14. A total of 39 sera with different clinical histories were used.

Sera

Group E 12 sera from 12 patients with no evidence of staphylococcal infection or colonization.
Group F 3 sera from 3 patients with diabetes and a foot ulcer colonized with the rifampicin resistant clone.
Group G 14 sera from 14 patients with positive cultures from either an intravenous line, sputum or wound swab who required systemic vancomycin and rifampicin therapy.
Group H 7 sera from patients who had recovered from a blood culture positive septicaemia.
Group I 3 sera from patients who had died from MRSA infection as proven by persistent positive blood cultures despite antibiotic therapy.

(1) 150 µl aliquots of peptide (10 µg/ml in 0.01M PBS) were pipetted into the wells of a Falcon 3912 microassay plate and were incubated overnight at 4° C.
(2) The unbound peptide was removed by washing four times (4×10 minutes) with 0.05% Tween 20 in 0.01 M PBS (pH 7.2).
(3) The plates were blocked with 2% skimmed milk-10% FCS in 0.01M PBS for 1 hour at 37° C.
(4) The plates were washed four times (4×10 minutes) with 0.05% Tween 20 in 0.01M PBS and the serum under investigation was added (1/100 dilution in blocking solution) into the wells of micro assay plate (three wells used for each serum) and incubated for 2 hours at 37° C.
(5) The plates were washed four times (4×10 minutes) with 0.05% Tween 20 in 0.01 M PBS and secondary antibody, anti-human IgM (or IgG) peroxidase conjugate (1/1000 dilution in blocking solution) was added and incubation proceeded for 1 hour at 37° C.
(6) The plates were washed four times (4×10 minutes) with 0.05% Tween 20 in 0.01 M PBS, followed by a further-washing with 0.01 M PBS. The plate was then incubated for 45 minutes at room temperature with agitation in 0.5 mg/ml of freshly prepared 2,2 Azino-bis[3-ethylbenz-thiazoline-6-sulfonic acid]diammonium (ABTS tablets) in pH 4.0 citrate buffer with 0.01% (w/v) hydrogen peroxide.
(7) Control wells were used in each plate. The three wells having ABTS solution only and three wells having ABTS solution plus anti-human IgG or IgM horseradish peroxidase conjugate only were used.
(8) Optical density (O.D.) measurements were made with an ELISA plate reader (Titertek Multiscan) at a wavelength of 405 nm.
(9) The average readings for each of three wells per patient's serum was determined.

The immunogenicity of Peptide 6 (SEQ ID NO: 18) carrying the epitope having the sequence of SEQ ID NO: 17 was tested by generating polyclonal rabbit antisera against peptide 6 using the protocol described above. Pre- and post-bleed sera were immunoblotted against the cloned and expressed ABC transporter protein, and showed seroconversion to the 67 kDa antigen.

Preparation of Phage Antibody Display Library and ScFv

The phage antibody display library and ScFv were produced essentially as previously described by Matthews, R. C. et al. (1995, J. Infect. Dis., 171: 1668–1671). Briefly, peripheral blood lymphocytes were obtained from a patient who had recovered from an EMRSA infection, by separation of 20 ml of heparinized blood over Ficoll. MRNA was extracted by guanidinium thiocyanate; this was followed by purification on an oligo(dT)-cellulose column (Quick Prep mRNA; Pharmacia, St. Albans, UK). First-strand cDNA synthesis was performed with a constant region primer for all four subclasses of human IgG heavy chains (HuIgG1-4) (Matthews, R. C. et al., 1994, Serodiagn. Immunother. Infect. Dis., 6: 213–217) using avian myeloblastosis virus reverse transcriptase (HT Biotechnology, Cambridge, UK). The heavy-chain variable-domain genes were amplified by primary PCRs with family-based forward (HuJH1-6) and backward (HuVH1a to 6a) primers. An Sfi1 restriction site was introduced upstream to the VH3a back-generated product, prior to assembly with a diverse pool of light-chain variable-domain genes. The latter also introduced a linker fragment ($Gly_4$ $SER_3$) and a downstream Not1 site. By use of the Sfi1 and NoI1 restriction enzyme sites, the product was undirectionally cloned into a phagemid vector. The ligated vector was introduced into *E. coil* TG1 by electroporation and phages were rescued with the helper phage M13K07 (Pharmacia). To enrich for antigen-specific scFv, the phage library was panned against peptides representing two of the epitopes delineated by epitope mapping, peptides 1 (SEQ ID NO: 6) and peptide 2 (SEQ ID NO: 7). Panning was performed in immunotubes coated with the corresponding peptide. Bound phages were eluted with log-phase *E.coli* TG1. After rescue with M13K07, the phages were repanned against peptide a further three times. BstN1 (New England Biolabs, Hiychen, UK) DNA fingerprinting was used to confirm enrichment of specific scFv after successive rounds of panning.

Animal Work

Experiment 1

30 female CD1 mice were given a bolus of $2\times10^6$ colony forming units (cfu) of EMRSA in the form of an IV injection. Two hours later, they were given either M13K07 ($10^8$ phage, 200 µl bolus, n=10), phage 12, $2\times10^8$ phage, 200 µl bolus, n=10) or phage 16 ($3.16\times10^8$ phage, 200 µl bolus, n=10). Colony counts of kidney, liver and spleen were performed on days 3 and 7 post-injection, the day of injection being considered Day 1.

Experiment 2

30 female CD1 mice were each given a 100 µl bolus of EMRSA containing $3\times10^7$ cfu. Two hours later, they were given either a negative phage super library ($7\times10^{10}$ phage, 200 µl bolus, n=10), phage 12 ($9\times10^7$ phage, 200 µl bolus, n=10) or phage 16 ($5\times10^8$ phage, 200 µl bolus, n=10). Colony counts of kidney, liver and spleen were performed on days 1 and 2.

Experiment 3

48 female CD1 mice were each given a 100 µl bolus of EMRSA containing $2\times10^7$ cfu. Two hours later, they were given either a negative phage ($10^8$ phage, 200 µl bolus, n=12), phage 12 ($10^8$ phage, 200 µl bolus, n=12, phage X ($10^7$ phage, 200 µl bolus, n=12) or phage 4 ($10^6$ phage, 200 µl bolus, n=12). Half the animals were culled and a second dose of phage given. The remaining animals were culled on day 2.

Experiment 4

45 female CD1 mice were each given a 100 µl bolus of EMRSA containing $2\times10^7$ cfu. Two hours later, they were given either a negative phage ($2.5\times10^7$ phage, 200 µl bolus, n=15) phage X ($3.3\times10^6$ phage, 200 µl bolus, n=15 or phage Y ($1.3\times10^6$ phage, 200 µl bolus, n=15). Five animals from each group were culled for colony counts on day 2 and the remaining 10 in each group on day 3).

Results

Epitope Mapping

Epitope mapping defined seven areas in residues 135–533 of the ABC transporter protein where patients were successfully treated for an EMRSA septicaemia. An area was designated as carrying an epitope if it produced three or more consecutive wells with a mean optical density (OD) at least 2 standard deviations above that of in-patient controls and that of the septicaemic patients who died (Table 3). The overlapping amino acid sequences were derived by a comparison of first and last peptide sequences. The sera from the colonised patients were also positive with some of the epitopes.

Indirect ELISA

Results for peptides 1–3 are given in Table 4. Results for peptides 4 and 5 are given in Table 10.

Conclusions

Colonised patients (Group B) recognised peptides 1 and 3 more than peptide 2. Peptide 3 was the least immunogenic. IgG against peptide 2 (Group C) was found in the patients who survived a septicaemia and not in colonised patients (Group B) and those who died (Group D). Results obtained for peptides 4 and 5 show a positive correlation between antibody against both peptides 4 and 5 and survival from systemic infection.

Human Recombinant Antibodies

These peptides were used to pan the phage antibody display library (above). Primary PCR amplification of the families of heavy-chain variable-domain genes showed amplification of VH3a alone, producing a 330-bp product which was assembled with the light-chain variable-domain gene library. BstNI fingerprints of the PCR-amplified scFv inserts before panning showed a highly heterogeneous library. After panning against Peptide 1, two BstN1 fingerprints predominated (X and Y) and after panning with Peptide 2, two further BstN1 fingerprints (12 and 16). These were selected for animal work.

Animal Work

Experiment 1

The colony counts are summarised in Table 5. Two mice spontaneously died in the group given clone 12 and 1 mouse from the group given clone 16 on day 1.

Conclusion

M13K07 (negative control) at day 3 gave similar results for the kidney whilst liver and spleen showed some activity with clones 12 and 16. At day 7 M13K07 and clone 16 gave similar results whilst clone 12 showed lower counts than M13K07 in kidney, liver and spleen.

Experiment 2

The colony counts are summarised in Table 6.

Conclusion

The super library (negative control) gave similar results to clone 16. Clone 12 had lower counts for kidney and spleen (day 1) and spleen and liver (day 2).

Experiment 3

The colony counts are summarised in Tables 7 and 8.

Conclusion

The negative phage produced similar counts to phage 12 (kidney, liver), phage X (liver, spleen) on day 1 and phage X (liver, spleen) on day 2. Phage Y was consistently positive and more positive than phage 12 with the exception of the kidney counts on day 2.

Experiment 4

The colony counts are summarised in Table 9.

Conclusion

The negative phage produced similar counts to phage X (kidney, spleen) on day 3 and phage Y (kidney on day 2). The other parameters showed a therapeutic response for phages X and Y with Y more active on both days 2 and 3 with the exception of the kidney count on day 2.

Overall Conclusions

Phages 12, X and Y all showed therapeutic activity, confirming the epitopes represented by peptides 1–5 as targets for antibody therapy.

TABLE 1

| Antigen apparent mol. weight (KDA) | Group 1 (n = 3) | | | | | | | | Group 2 (n = 3) | | | | | | | |
|---|---|---|---|---|---|---|---|---|---|---|---|---|---|---|---|---|
| | VS RS | | VR RS | | VS RR | | VR RR | | VS RS | | VR RS | | VS RR | | VR RR | |
| | M | G | M | G | M | G | M | G | M | G | M | G | M | G | M | G |
| 140 | 0 | 0 | 0 | 0 | 2 | 2 | 0 | 0 | 0 | 0 | 0 | 0 | 3 | 3 | 0 | 0 |
| 120 | 0 | 1 | 0 | 1 | 0 | 1 | 0 | 1 | 0 | 0 | 0 | 0 | 0 | 0 | 0 | 0 |
| 84 | 0 | 0 | 0 | 0 | 0 | 0 | 0 | 0 | 0 | 0 | 0 | 0 | 0 | 0 | 0 | 0 |
| 69 | 0 | 0 | 0 | 0 | 0 | 0 | 0 | 0 | 2 | 2 | 2 | 2 | 2 | 2 | 1 | 2 |
| 67 | 2 | 2 | 2 | 2 | 2 | 2 | 0 | 3 | 3 | 2 | 3 | 2 | 3 | 3 | 2 | 2 |
| 60 | 0 | 2 | 1 | 2 | 1 | 2 | 1 | 2 | 1 | 1 | 1 | 1 | 1 | 1 | 1 | 1 |
| 53 | 0 | 2 | 0 | 1 | 0 | 2 | 0 | 2 | 0 | 0 | 1 | 0 | 2 | 2 | 3 | 3 |
| 42 | 0 | 3 | 0 | 1 | 0 | 3 | 0 | 1 | 0 | 0 | 2 | 2 | 0 | 0 | 0 | 1 |
| 37 | 0 | 0 | 0 | 0 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 | 0 | 0 | 0 | 0 |
| 27 | 0 | 0 | 1 | 1 | 0 | 0 | 0 | 0 | 0 | 0 | 0 | 1 | 0 | 0 | 0 | 0 |

TABLE 2

| Antigen apparent mol. weight (KDa) | Group 3 | | | | | | | | Group 4 | | | | | | | |
|---|---|---|---|---|---|---|---|---|---|---|---|---|---|---|---|---|
| | VS RS | | VR RS | | VS RR | | VR RR | | VS RS | | VR RS | | VS RR | | VR RR | |
| | M | G | M | G | M | G | M | G | M | G | M | G | M | G | M | G |
| 140 | 0 | 0 | 0 | 0 | 2 | 3 | 0 | 0 | 0 | 0 | 0 | 0 | 3 | 5 | 0 | 0 |
| 120 | 0 | 1 | 0 | 1 | 0 | 1 | 0 | 1 | 0 | 2 | 0 | 2 | 0 | 2 | 0 | 1 |
| 84 | 0 | 0 | 0 | 0 | 0 | 0 | 0 | 0 | 1 | 1 | 1 | 1 | 1 | 1 | 0 | 1 |
| 69 | 0 | 0 | 0 | 0 | 0 | 0 | 0 | 0 | 1 | 1 | 1 | 1 | 1 | 1 | 1 | 1 |
| 67 | 1 | 3 | 1 | 3 | 1 | 3 | 1 | 3 | 3 | 5 | 3 | 5 | 4 | 5 | 3 | 5 |
| 60 | 1 | 1 | 1 | 1 | 1 | 1 | 1 | 1 | 2 | 0 | 2 | 0 | 2 | 0 | 2 | 0 |
| 53 | 1 | 2 | 1 | 2 | 1 | 2 | 2 | 3 | 2 | 3 | 2 | 3 | 2 | 3 | 1 | 3 |
| 42 | 0 | 1 | 0 | 1 | 0 | 1 | 0 | 1 | 2 | 3 | 1 | 2 | 2 | 3 | 1 | 2 |
| 37 | 0 | 1 | 0 | 1 | 0 | 2 | 0 | 2 | 0 | 1 | 0 | 1 | 0 | 1 | 0 | 1 |
| 30 | 0 | 0 | 0 | 0 | 0 | 0 | 0 | 0 | 0 | 0 | 1 | 2 | 1 | 1 | 1 | 3 |

TABLE 3

| Well No. | Epitope SEQ ID NO: | Hospital in-patient controls (n = 2) | Colonised patients (n = 5) | Septicaemia patients who died (n = 4) | Septicaemia patients who survived (n = 4) |
|---|---|---|---|---|---|
| 64 | 9 | 0.476(0.393) | 0.815(0.281) | 0.547(0.249) | 0.823(0.547) |
| 65 | 9 | 0.480(0.316) | 0.972(0.329) | 0.568(0.244) | 1.131(0.351) |
| 66 | 9 | 0.521(0.359) | 1.051(0.276) | 0.610(0.243) | 1.350(0.625) |
| 67 | 9 | 0.416(0.304) | 0.855(0.199) | 0.511(0.213) | 1.164(0.545) |
| 86 | 3 | 0.484(0.358) | 0.932(0.253) | 0.531(0.206) | 1.313(0.614) |
| 87 | 3 | 0.490(0.359) | 0.997(0.292) | 0.560(0.236) | 1.232(0.483) |
| 88 | 3 | 0.649(0.427) | 0.923(0.251) | 0.581(0.167) | 1.308(0.410) |

TABLE 3-continued

| Well No. | Epitope SEQ ID NO: | Hospital in-patient controls (n = 2) | Colonised patients (n = 5) | Septicaemia patients who died (n = 4) | Septicaemia patients who survived (n = 4) |
|---|---|---|---|---|---|
| 89 | 3 | 0.663(0.231) | 1.027(0.260) | 0.780(0.110) | 1.235(0.479) |
| 90 | 3 | 0.833(0.402) | 1.057(0.279) | 0.679(0.109) | 1.522(0.551) |
| 91 | 3 | 0.843(0.421) | 1.108(0.272) | 0.869(0.278) | 1.533(0.545) |
| 153 | 4 | 0.670(0.368) | 1.16(0.179) | 0.782(0.251) | 1.526(0.551) |
| 154 | 4 | 0.578(0.219) | 1.1189(0.204) | 0.863(0.287) | 1.748(0.460) |
| 155 | 4 | 0.653(0.227) | 1.216(0.186) | 0.779(0.254) | 1.917(0.509) |
| 156 | 4 | 0.635(0.243) | 0.98(0.127) | 0.805(0.230) | 1.593(0.461) |
| 157 | 4 | 0.667(0.374) | 1.176(0.241) | 0.836(0.292) | 1.761(0.649) |
| 158 | 4 | 0.683(0.274) | 1.147(0.222) | 0.765(0.191) | 1.774(0.563) |
| 211 | 10 | 0.439(0.176) | 0.752(0.62) | 0.495(0.125) | 1.145(0.502) |
| 212 | 10 | 0.581(0.207) | 0.802(0.087) | 0.669(0.167) | 1.360(0.384) |
| 213 | 10 | 0.582(0.197) | 0.923(0.127) | 0.663(0.157) | 1.351(0.374) |
| 214 | 10 | 0.587(0.219) | 0.949(0.126) | 0.680(0.186) | 1.506(0.570) |
| 233 | 11 | 0.447(0.257) | 0.937(0.148) | 0.496(0.193) | 1.091(0.512) |
| 234 | 11 | 0.589(0.441) | 0.970(0.145) | 0.543(0.186) | 1.129(0.44) |
| 235 | 11 | 0.551(0.341) | 1.015(0.126) | 0.585(0.213) | 1.448(0.626) |
| 255 | 12 | 0.492(0.357) | 0.970(0.156) | 0.513(0.181) | 1.280(0.509) |
| 256 | 12 | 0.520(0.407) | 1.011(0.18) | 0.548(0.194) | 1.219(0.463) |
| 257 | 12 | 0.596(0.488) | 1.054(0.225) | 0.576(0.173) | 1.296(0.433) |
| 258 | 12 | 0.414(0.326) | 1.010(0.243) | 0.505(0.173) | 1.046(0.476) |
| 259 | 12 | 0.571(0.538) | 0.746(0.238) | 0.598(0.201) | 1.308(0.497) |
| 272 | 5 | 0.613(0.430) | 1.105(0.20) | 0.640(0.203) | 1.502(0.582) |
| 273 | 5 | 0.603(0.420) | 1.059(0.181) | 0.649(0.234) | 1.464(0.576) |
| 274 | 5 | 0.752(0.439) | 1.200(0.306) | 0.775(0.233) | 1.695(0.640) |
| 275 | 5 | 0.698(0.444) | 1.289(0.238) | 0.801(0.278) | 1.699(0.586) |
| 276 | 5 | 0.750(0.301) | 1.286(0.245) | 0.876(0.229) | 1.860(0.696) |
| 277 | 5 | 0.739(0.297) | 1.272(0.25) | 0.823(0.261) | 1.739(0.690) |

TABLE 4

| | Groups | | | |
|---|---|---|---|---|
| | A n = 12 | B n = 6 | C n = 3 | D n = 3 |
| Peptide 1 | | | | |
| IgM > 0.4 | 0 | 5 | 1 | 1 |
| IgG > 0.3 | 2 | 5 | 3 | 3 |
| Peptide 2 | | | | |
| IgM > 0.4 | 2 | 2 | 1 | 1 |
| IgG > 0.3 | 0 | 1 | 3 | 0 |
| Peptide 3 | | | | |
| IgM > 0.3 | 0 | 2 | 0 | 0 |
| IgG > 0.2 | 0 | 3 | 0 | 1 |

TABLE 5

| | | M13K07 | | | Clone 12 | | | Clone 16 | | |
|---|---|---|---|---|---|---|---|---|---|---|
| | | Kidney | Liver | Spleen | Kidney | Liver | Spleen | Kidney | Liver | Spleen |
| | | (n = 5) | | | (n = 5) | | | (n = 5) | | |
| Day 3 | | $3.7 \times 10^7$ | $8.9 \times 10^4$ | $8.7 \times 10^4$ | $1.5 \times 10^9$ | $5.3 \times 10^3$ | $6.8 \times 10^3$ | $1.7 \times 10^7$ | $5 \times 10^3$ | $3 \times 10^3$ |
| | | (n = 5) | | | (n = 3) | | | (n = 4) | | |
| Day 7 | | $1.7 \times 10^7$ | $1.1 \times 10^6$ | $3.1 \times 10^3$ | $5.1 \times 10^6$ | $2.9 \times 10^4$ | $2 \times 10^3$ | $5.4 \times 10^7$ | $5.5 \times 10^3$ | $4 \times 10^3$ |

TABLE 6

| | Super Library | | | Clone 12 | | | Clone 16 | | |
|---|---|---|---|---|---|---|---|---|---|
| | Kidney | Liver | Spleen | Kidney | Liver | Spleen | Kidney | Liver | Spleen |
| | (n = 5) | | | (n = 5) | | | (n = 5) | | |
| Day 3 | $7.2 \times 10^5$ | $1.7 \times 10^4$ | $6.1 \times 10^5$ | $5.8 \times 10^5$ | $1.6 \times 10^4$ | $5.4 \times 10^4$ | $1.0 \times 10^8$ | $1 \times 10^4$ | $1.6 \times 10^4$ |
| | (n = 5) | | | (n = 5) | | | (n = 5) | | |
| Day 2 | $2.6 \times 10^7$ | $8.3 \times 10^3$ | $6.6 \times 10^4$ | $3.2 \times 10^7$ | $4 \times 10^3$ | $2.6 \times 10^4$ | $1.4 \times 10^7$ | $1.1 \times 10^4$ | $2.8 \times 10^4$ |

TABLE 7

| | Negative Phage | | | Phage 12 | | |
|---|---|---|---|---|---|---|
| | Kidney | Liver | Spleen | Kidney | Liver | Spleen |
| | (n = 6) | | | (n = 6) | | |
| Day 1 | $8.1 \times 10^6$ | $1.5 \times 10^4$ | $1.2 \times 10^5$ | $6.5 \times 10^6$ | $5 \times 10^4$ | $9 \times 10^4$ |
| Day 2 | $3 \times 10^8$ | $8.4 \times 10^4$ | $2.9 \times 10^5$ | $3 \times 10^8$ | $1.5 \times 10^5$ | $3 \times 10^4$ |

TABLE 8

| | Phage X | | | Phage Y | | |
|---|---|---|---|---|---|---|
| | Kidney | Liver | Spleen | Kidney | Liver | Spleen |
| | (n = 6) | | | (n = 6) | | |
| Day 1 | $4.7 \times 10^5$ | $9.8 \times 10^4$ | $1.5 \times 10^5$ | $9.1 \times 10^5$ | $8.3 \times 10^3$ | $8 \times 10^4$ |
| Day 2 | $1.5 \times 10^7$ | $5 \times 10^4$ | $1 \times 10^5$ | $1 \times 10^7$ | $1.7 \times 10^4$ | $2 \times 10^4$ |

TABLE 9

| | Negative phage | | | Clone X | | | Clone Y | | |
|---|---|---|---|---|---|---|---|---|---|
| | Kidney | Liver | Spleen | Kidney | Liver | Spleen | Kidney | Liver | Spleen |
| | (n = 5) | | | (n = 5) | | | (n = 5) | | |
| Day 2 | $1.7 \times 10^7$ | $3.2 \times 10^4$ | $4.5 \times 10^4$ | $4 \times 10^6$ | $4.8 \times 10^3$ | $2.7 \times 10^4$ | $1.3 \times 10^7$ | $1.6 \times 10^4$ | $1.4 \times 10^4$ |
| | (n = 10) | | | (n = 10) | | | (n = 10) | | |
| Day 3 | $6.7 \times 10^7$ | $1.7 \times 10^5$ | $1.6 \times 10^5$ | $9.4 \times 10^7$ | $5.4 \times 10^4$ | $1.2 \times 10^5$ | $4.7 \times 10^7$ | $3.2 \times 10^4$ | $5 \times 10^4$ |

TABLE 10

| | Peptide 4 | | Peptide 5 | |
|---|---|---|---|---|
| | IgM | IgG | IgM | IgG |
| Control sera n = 12 (Group E) | 4 | 1 | 2 | 0 |
| Colonised foot ulcer n = 3 (Group F) | 1 | 0 | 1 | 0 |
| IV line, Sputum, Wound Swab[a] n = 14 (Group G) | 6 | 9 | 7 | 8 |
| Systemic[a] survived n = 7 (Group H) | 3 | 6 | 3 | 5 |
| Systemic[a] died n = 3 (Group I) | 0 | 0 | 0 | 0 |

What is claimed is:

1. An isolated Staphylococcal ABC transporter protein as set forth in SEQ ID NO:2.

2. An isolated peptide consisting of a fragment of a Staphylococcal ABC transporter protein selected from the group consisting of SEQ ID NO: 3–14, 17 and 18.

3. A diagnostic test kit for Staphylococci, comprising: an isolated Staphylococcal ABC transporter protein according to claim 1, or an isolated peptide according to claim 2.

4. An isolated peptide according to claim 2 having SEQ ID NO:3.

5. An isolated peptide according to claim 2 having SEQ ID NO:4.

6. An isolated peptide according to claim 2 having SEQ ID NO:5.

7. An isolated peptide according to claim 2 having SEQ ID NO:6.

8. An isolated peptide according to claim 2 having SEQ ID NO:7.

9. An isolated peptide according to claim 2 having SEQ ID NO:8.

10. An isolated peptide according to claim 2 having SEQ ID NO:9.

11. An isolated peptide according to claim 2 having SEQ ID NO:10.

12. An isolated peptide according to claim 2 having SEQ ID NO:11.

13. An isolated peptide according to claim 2 having SEQ ID NO:12.

14. An isolated peptide according to claim 2 having SEQ ID NO:13.

15. An isolated peptide according to claim 2 having SEQ ID NO:14.

16. An isolated peptide according to claim 2 having SEQ ID NO:17.

17. An isolated peptide according to claim 2 having SEQ ID NO:18.

* * * * *